United States Patent [19]

von Itter et al.

[11] Patent Number: 5,041,619

[45] Date of Patent: Aug. 20, 1991

[54] PROCESS FOR THE PREPARATION OF ALKOXYALKYLIDENEMALONIC ACID ESTERS

[75] Inventors: Franz-Albert von Itter, Bonn; Klaus-Dieter Steffen, Hennef, both of Fed. Rep. of Germany

[73] Assignee: Huels Aktiengesellschaft, Marl, Fed. Rep. of Germany

[21] Appl. No.: 552,902

[22] Filed: Jul. 16, 1990

[30] Foreign Application Priority Data

Aug. 23, 1989 [DE] Fed. Rep. of Germany ....... 3927761

[51] Int. Cl.$^5$ ...................... C07C 69/73; C07C 69/76
[52] U.S. Cl. ...................................... 560/181; 560/60
[58] Field of Search ................................. 560/181, 60

[56] References Cited

U.S. PATENT DOCUMENTS 4,738,796  4/1988  Ratton ................................. 252/400

FOREIGN PATENT DOCUMENTS 2068116  6/1977  Japan .
1100147  4/1989  Japan .

Primary Examiner—Paul J. Killos
Attorney, Agent, or Firm—Oblon, Spivak, McClelland, Maier & Neustadt

[57] ABSTRACT

A process for the preparation of alkoxyalkylidenemalonic acid esters. The reaction is catalyzed by easily separable, insoluble aluminum silicates.

14 Claims, No Drawings

PROCESS FOR THE PREPARATION OF ALKOXYALKYLIDENEMALONIC ACID ESTERS

BACKGROUND OF THE INVENTION

1. Field of the Invention

The invention relates to a process for the preparation of dialkyl alkoxyalkylidenemalonates by reaction of malonic acid esters with trialkyl orthocarboxylates. Alkoxyalkylidenemalonic malonic acid esters are important intermediates for the synthesis of various substituted quinolines which are employed as pharmaceuticals against malaria or bacterial infections.

2. Discussion of the Background

The preparation of the alkoxyalkylidenemalonic acid esters from malonic acid esters and orthocarboxylic acid esters is known. The condensation is carried out in acetic anhydride using $ZnCl_2$ as catalyst according to L. Claisen, Berichte 26, 2729 (1893).

Since then, various improvements to this route of preparation have been put forward with the aim of increasing the yields and the productivity of the reaction.

According to DE 2,426,964, the reaction of dialkyl malonate with an excess of trialkyl orthoformate is carried out in the presence of sub-stoichiometric amounts of acetic anhydride and Lewis acids such as zinc salts, aluminum salts or iron salts as catalyst For the preparation of diethyl ethoxymethylenemalonate, a yield of 94% of the theoretical yield based on malonic ester is mentioned. The preparation of dimethyl methoxymethylenemalonate is carried out under analogous conditions with a yield of 70% of the theoretical yield and, at a pressure of 3 bar, with a yield of 86% based on the malonic acid ester. These yields are not satisfactory. As a result of the incomplete conversion, purities of only 94 are obtained.

If, as described in U.S. Pat. No. 2,824,121, the preparation of diethyl ethoxymethylenemalonate is carried out by reaction of diethyl malonate with triethyl orthoformate in the absence of Lewis acids using acetic acid as the only catalyst, a yield of 91.8%, based on reacted diethyl malonate, with a conversion of only 60%, is achieved.

In EP 0,152,319, the reaction of diethyl malonate with triethyl orthoformate is catalysed by salts of Cd, Hg, Bi and Mg. The yields of diethyl ethoxymethylenemalonate determined by gas chromatography are very high. However, they do not correspond to the yields practically attainable by isolation of the product.

The Cd, Hg and Bi salts additionally lead to heavy metal-containing product residues. The disposal of these residues is increasingly difficult and cost-intensive. Also, from ecological points of view, a substitution of the metal salts appears desirable. The contamination of the alkoxyalkylidenemalonic esters with such toxic metal salts may limit their use as pharmaceutical precursors or even make it impossible.

The known catalysts moreover yield dimethyl methoxymethylenemalonate in unsatisfactory yields in the reaction of the less active trimethyl orthoformate with dimethyl malonate.

SUMMARY OF THE INVENTION

Accordingly, one object of the invention is a process for the preparation of alkoxyalkylidenemalonic acid esters which leads, by means of a simple reaction, to good yields and conversions without the use of heavy metal-containing catalysts. In particular, improved yield and conversion in the preparation of dimethyl methoxymethylenemalonate and diethyl ethoxymethylenemalonate are also specific objects of the invention.

This and other objects which will become apparent from the following specification have been achieved by employing aluminum silicates as catalysts in the preparation of alkoxyalkylidenemalonic acid esters of the formula

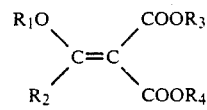

in which $R_1$ is alkyl having 1 to 4 carbon atoms, $R_2$ is hydrogen, alkyl having 1 to 4 carbon atoms, aryl, aralkyl or alkoxy and $R_3$ and $R_4$ are alkyl having 1 to 4 carbon atoms, from malonic esters of the formula $R_3OOCCH_2COOR_4$ and orthocarboxylic acid esters of the formula $R_2(OR_1)_3$ in the presence of carboxylic acids or their anhydrides. The groups $R_1$, $R_3$ and $R_4$ may in this case be identical or different.

Preferred aryl groups for $R_2$ are aryl groups having 6-10 carbon atoms, for example phenyl and naphthyl groups. If desired, the aryl group may be substituted with one or more alkyl groups having from 1-4 carbon atoms. Preferred aralkyl groups contain 7-10 carbon atoms, for example benzyl or other alkylphenyl groups. Preferred alkoxy groups are alkoxy groups having 1-4 carbon atoms.

A preferred embodiment is a process for the preparation of products of the formula (I), in which $R_1$, $R_3$ and $R_4$ are identical and $R_2$ is hydrogen or alkyl having 1 to 4 carbon atoms. The invention very particularly relates to the preparation of dimethyl methoxymethylenemalonate and diethyl ethoxymethylenemalonate.

The aluminum silicates employed as catalysts are preferably clay minerals, very preferably montmorillonite or montmorillonite-containing layer silicates such as, for example, bentonites, smectites or attapulgite.

In order to increase their activity, the catalysts can be treated with acids or acidic salts, preferably with mineral acids such as, for example, sulphuric acid or phosphoric acid. Thus, for example, bentonites treated with $H_2SO_4$ or $H_3PO_4$ can be used. Typical acidic salts are, for example, sodium and potassium hydrogen sulphates or hydrogen phosphates. Activation of the catalysts can also be carried out during the reaction by addition of the acidic salts or acids continuously or in portions. Increases in activity generally lead to improved conversions.

If these acids or acidic salts are used without the catalysts, the necessary reaction times are lengthened considerably with a simultaneously clearly reduced yield.

The amount of the catalyst employed is in general about 0.001 g to about 10 g per mole of malonate. The preferred range is 0.01 g to 1 g per mole of malonate. The water adhering to the commercial clay minerals can be largely removed by customary drying methods such as heating in vacuo. Since the orthoesters employed in the reaction also act as drying agents, the commercial products can also be used directly. The addition of the catalysts can be carried out by known methods.

The aluminum silicate catalysts can also be employed in combination with metal salt catalysts which are customarily used.

The reaction temperature is preferably about 60° to 200° C. A temperature range of 100° to 170° C. is very particularly preferred.

During the reaction, a pressure of about 1 to 10 bar is preferably set. A pressure of 1 to 3 bar is particularly preferred.

The carboxylic acids and their anhydrides employed as additional condensing agents are preferably lower aliphatic carboxylic acids having 1 to 5 carbon atoms or the corresponding anhydrides. The amount employed is in general about 0.01 to 1 mole per mole of malonate.

The orthocarboxylic acid ester can be used in the process stoichiometrically or in excess. The amount employed is preferably 1 to 6 moles per mole of malonic acid ester. 1.2 to 4 moles of orthocarboxylic acid ester per mole of malonic acid ester are particularly preferred.

The orthocarboxylic acid ester may also be partially replaced by solvents boiling in the same temperature range. Solvents of this type are, for example, aromatic hydrocarbons or high-boiling ethers. By means of these solvents, the excess orthocarboxylic acid esters can be somewhat reduced.

The reaction is carried out most simply by adding together the reactants and the catalysts in the above-mentioned ratios and reacting at the described temperatures. Preferrably, malonic acid ester, orthoester and the mineral catalyst are initially introduced with a partial amount of the carboxylic acid and/or anhydride and the residual amounts of the carboxylic acid and/or anhydride are added continuously or in portions corresponding to the course of the reaction. It is likewise possible also to bring only a partial amount of the orthoester to reaction with the other starting compounds corresponding to the above-mentioned processes and to meter in the other part continuously or in portions during the reaction.

The alcohol eliminated in the condensation is advantageously removed continuously by distillation. After complete reaction of the malonic acid ester, it is desirable to leave the reaction mixture at the reaction temperature until extensive conversion of the intermediates formed, such as bis-alkoxy-alkylmalonic acid esters, to the alkoxyalkylidenemalonic acid esters has taken place. In order to complete the reaction, further catalytic amounts of about 0.05 to 0.5% by weight, based on the malonic acid ester employed, of carboxylic acid anhydrides and/or inorganic or organic acids such as, for example, sulphuric acid, phosphoric acid, citric acid and p-toluenesulphonic acid or of acidic salts such as, for example, potassium hydrogen sulphate can be optionally added to the reaction mixture, after separating off the mineral catalyst The mixture is then kept at a temperature of 100° to 180° C. for 1 to 5 hours. By this means, for example, the product purity of dimethyl methoxymethylenemalonate can be increased to above 98%.

The process can be carried out at normal pressure and elevated pressure. The particularly preferred reaction temperatures are in the range from 100° to 170° C., with the maximum attainable reaction temperature at normal pressure being limited, however, by the boiling points of the components. Working under pressure makes possible an increase in the reaction temperature to the optimum values and thus an increase in the reaction rate This leads to clearly improved space/time yields. In particular when using the relatively low-boiling orthoesters, such as, for example, trimethyl orthoformate or trimethyl orthoacetate, the reaction and post-reaction times can be shortened and, as a result of lowered by-product formation, the yields further increased.

After completion of the reaction, the excess orthoester is preferably separated off by distillation at reduced pressure. This orthoester can be fed back or recycled to further batches.

It is advantageous to remove the catalyst before the distillation. The aluminum silicates of the invention have advantages here compared to the metal salts used hitherto, since they are insoluble and can be separated off without problems by filtration or sedimentation without other manipulations.

Aluminum silicate catalysts which have been filtered off can additionally be employed again after washing with the corresponding orthoester. In this way, the material and disposal costs are reduced.

The catalysts show high activity and selectivity under the reaction conditions and permit a virtually quantitative conversion of the malonic acid esters. It is thus now possible to obtain even dimethyl methoxymethylenemalonate in yields of above 92% of the theoretical yield, based on the malonic acid ester employed. In the synthesis of diethyl ethoxymethylenemalonate, yields of 95% of isolated product are obtained. It is thus possible, with the aid of easily separable aluminum silicates, to eliminate the heavy metal salts used hitherto.

Having generally described this invention, a further understanding can be obtained by reference to certain specific examples which are provided herein for purposes of illustration only and are not intended to be limiting unless otherwise specified.

EXAMPLES

EXAMPLE 1

264.2 g (2.0 mol) of dimethyl malonate, 637 g (6 mol) of trimethyl orthoformate and 20.4 g (0.2 mol) of acetic anhydride containing 2 g of $H_2SO_4$-activated bentonite (montmorillonite catalyst KSF/O from Sud-Chemie, D-8000 Munich) were initially introduced into a reaction flask provided with a stirrer, thermometer, dropping funnel, column and reflux condensor, and the mixture was heated to boiling. 40.8 g (0.4 mol) of acetic anhydride were continuously metered in during the course of 6 hours. The low boiling component formed was distilled off at a head temperature of 62° to 67° C. The bottom temperature increased slowly from 109° to 133° C. After 8 hours, the excess orthoester was distilled off at reduced pressure. 40.8 g (0.4 mol) of acetic anhydride were added to the remaining reaction mixture and the mixture was heated at 140° C. for 2 hours. The catalyst was then filtered off and the crude product was distilled in vacuo. 330.4 g of dimethyl methoxymethylenemalonate (98% pure) having a melting point of 44° to 46° C. were obtained at 0.5 mbar and a head temperature of 110° C. This corresponds to a yield of 92% of theoretical yield.

EXAMPLE 2

330.3 g (2.5 mol) of dimethyl malonate, 1078 g (10.2 mol) of trimethyl orthoformate, 15 g of acetic anhydride and 1 g of catalyst from Example 1 were put into a glass autoclave having a pressure distillation section, stirrer, temperature measuring sites, safety valves and a metering pump. The sealed apparatus was heated to 120° C., whereupon an internal pressure of 1.95 bar built up. 36 g of acetic anhydride were then metered in 3 g portions over the course of 5 hours. The internal temperature increased slowly to 155° C. The low-boiling components formed distilled off at a head temperature of 91° to 92° C.

After a total reaction time of 7.5 hours, the mixture was cooled, the catalyst was filtered off and the excess of trimethyl orthoformate was distilled off under a slight vacuum. After adding 3 drops of $H_3PO_4$, the mixture was then heated at 140° C. for 2 hours and the crude product distilled over at 0.5 mbar and a head temperature of 110° C. 406 g of dimethyl methoxymethylenemalonate (98.6% pure) were obtained, which corresponds to a yield of 91.9% of the theoretical yield.

COMPARISON EXAMPLE A

The batch from Example 2 was repeated, 0.25 g of conc. $H_2SO_4$ being employed as catalyst and the reaction time being increased to 12 hours. After distillation of the crude product, 360 g of dimethyl methoxymethylenemalonate having a purity of 97% were obtained, which corresponds to a yield of 80% of the theoretical yield.

EXAMPLE 3

160.2 g (1.0 mol) of diethyl malonate, 474.2 g (3.2 mol) of triethyl orthoformate, 4 g of acetic anhydride and 0.5 g of catalyst from Example 1 were initially introduced into the apparatus described in Example 1 and the mixture was heated to boiling. A mixture of 10 g of acetic anhydride and 30 g of triethyl orthoformate were continuously added dropwise in the course of 6 hours. The low-boiling component formed was distilled off at a head temperature of 78° to 79° C. The reaction temperature slowly increased to 159° C. The mixture was kept at this temperature for a further hour. The unreacted orthoester was then distilled off at reduced pressure, the catalyst was filtered off and the crude product was purified by distillation at 0.5 mbar. In this way 205.6 g of diethyl ethoxymethylenemalonate were obtained, which corresponds to a yield of 95.1% of the theoretical yield.

EXAMPLE 4

The batch from Example 3 was repeated, 0.5 g of $H_3PO_4$-activated bentonite (montmorillonite catalyst KP 10 from Sud-Chemie, D-8000 Munich) being employed as catalyst. After distillation, 204.7 g of diethyl ethoxymethylenemalonate were obtained, which corresponds to a yield of 94.7% of the theoretical yield.

EXAMPLE 5

The batch from Example 3 was repeated, 0.5 g of bentonite (montmorillonite catalyst K 10 from Sud-Chemie, D-8000 Munich) being employed as catalyst. After distillation, diethyl ethoxymethylenemalonate was obtained in a yield of 76.8% of theory and diethyl diethoxymethylenemalonate in a yield of 18.2% of the theoretical yield.

EXAMPLE 6

160.2 g (1.0 mol) of diethyl malonate, 474.2 g (3.2 mol) of triethyl orthoformate and 0.5 g of catalyst from Example 5 were initially introduced and the mixture was heated to boiling. A mixture of 10 g of acetic anhydride, 1 g of $H_3PO_4$ and 30 g of triethyl orthoformate were continuously added dropwise over the course of 6 hours. The reaction and work up were carried out in accordance with Example 3 and gave 200 g of diethyl ethoxymethylenemalonate, which corresponds to a yield of 92.6% of the theoretical yield.

EXAMPLE 7

264 g (2 mol) of dimethyl malonate, 961 g (8 mol) of trimethyl orthoacetate and 1 g of catalyst from Example 1 were put into the pressure apparatus described in Example 2. The mixture was heated to 130° C., whereupon an internal pressure of 1.5 bar developed. 100 g of acetic anhydride were then metered in over the course of 12 hours, the low-boiling component was distilled off at a head temperature of 82° to 87° C. and the reaction temperature was gradually increased to 160° C. After complete distillation of the low-boiling component, the mixture was cooled, the excess trimethyl orthoacetate distilled off at reduced pressure and the crude product was fractionated through a short column at a head temperature of 110° C. under a high vacuum of 0.3 mbar. In this way methyl 2-carbomethoxy-3-methoxy-2-butenoate was obtained in a yield of 77.5% and methyl 2-carbomethoxy-3,3-dimethoxy-butanoate was obtained in a yield of 11% of the theoretical yield.

EXAMPLE 8

160 g (1 mol) of diethyl malonate, 649 g (4 mol) of triethyl orthoacetate and 0.5 g of catalyst from Example 1 were heated to 130° C. in a glass apparatus having a distillation column. The metering-in of 102 g of acetic anhydride over the course of 7 h was then begun. The bottom temperature was increased to 159° C. with the distillation of low-boiling components at a head temperature of 72° to 73° C. After the end of the reaction, the residual low-boiling components were distilled off under a low vacuum and the excess triethyl orthoacetate was removed at 15 mbar. The desired product was then distilled over at 0.3 mbar and a head temperature of 100° to 102° C. Ethyl 2-carboethoxy-3-ethoxy-2-butenoate was obtained in a yield of 73% of the theoretical yield.

EXAMPLE 9

188 g (1 mol) of diisopropyl malonate, 571 g (3 mol) of triisopropyl orthoformate and 0.05 g of catalyst from Example 5 were initially introduced into the apparatus mentioned in Example 1 and the mixture was heated to 110° C. 102 g of acetic anhydride were then metered in over the course of 5 hours. The bottom temperature was raised to 150° C. At the same time a low-boiling fraction was removed under reflux at a boiling temperature of 60° C. After 10 hours, the formation of low-boiling component decreased. The mixture was then fractionated in vacuo, first at 15 mbar and then at 0.3 mbar. 7.6% of diisopropyl malonate, 80.2% of diisopropyl isopropoxymethylenemalonate and 6.5% of diisopropyl diisopropoxy-methylmalonate were obtained. The last-mentioned compound was converted into diisopropyl isopropoxymethylenemalonate by heating with 0.2 g of $H_3PO_4$.

Obviously, numerous modifications and variations of the present invention are possible in light of the above teachings. It is therefore to be understood that within the scope of the appended claims, the invention may be

What is claimed as new and desired to be secured by Letters Patent of the United States is:

1. A process for the preparation of a dialkyl alkoxyalkylidenemalonate of the formula

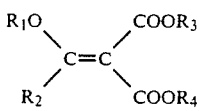

wherein
$R_1$ is $C_{1-4}$ alkyl,
$R_2$ is hydrogen, $C_{1-4}$ alkyl, aryl, aralkyl or alkoxy and
$R_3$ and $R_4$ are $C_{1-4}$ alkyl, comprising reacting a dialkylmalonate of the formula $R_3OOCCH_2COOR_4$ with a trialkyl orthocarboxylate of the formula $R_2C(OR_1)_3$ in the presence of a carboxylic acid, carboxylic acid anhydride, or mixture thereof and an aluminum silicate catalyst.

2. The process of claim 1, wherein $R_1$, $R_3$ and $R_4$ are identical and $R_2$ is hydrogen or $C_{1-4}$ alkyl.

3. The process of claim 2, wherein $R_1$, $R_3$ and $R_4$ are identical and are methyl or ethyl and $R_2$ is hydrogen.

4. The process of claim 1, wherein said aluminum silicate is in the form of a clay mineral.

5. The process of claim 4, wherein said clay mineral is a montmorillonite or montmorillonite-containing layer silicate.

6. The process of claim 1, wherein said aluminum silicate is aluminum silicate treated with a mineral acid, acidic salt or mixture thereof.

7. The process of claim 6, wherein the mineral acid is added to the reaction mixture continuously or in portions before or during the reacting step.

8. The process of claim 1, wherein the amount of the catalyst is about 0.001 g to 10 g per mole of dialkylmalonate.

9. The process of claim 1, wherein the temperature of the reacting step is about at 60° to 200° C.

10. The process of claim 1, wherein the reacting step is carried out at a pressure of about 1 to 10 bar.

11. The process of claim 1, wherein the amount of carboxylic acid or carboxylic acid anhydride is about 0.01 to 1 mole per mole of dialkylmalonate.

12. The process of claim 1, wherein the amount of trialkyl orthocarboxylate is 1 to 6 moles per mole of dialkylmalonate.

13. The process of claim 1, further comprising adding 0.05 to 0.5% by weight, based on the dialkylmalonate of a carboxylic acid anhydride, inorganic acid, inorganic acid salt, organic acid, or organic acid salt to the reaction mixture after said reacting step, and heating at a temperature of 100° to 180° C.

14. The process of claim 13, wherein the catalyst is separated from the reaction mixture prior to said adding step.

* * * * *